(12) United States Patent
Keller et al.

(10) Patent No.: US 6,498,496 B1
(45) Date of Patent: Dec. 24, 2002

(54) DEVICE FOR DETECTING MEMBRANE LEAKS IN A DIAPHRAGM PUMP

(75) Inventors: Heinz Keller, Birkenau/Niederliebersb (DE); Gerhard Rohner, Hemsbach (DE); Jens Plechinger, Weinheim (DE); Hans-Juergen Diekmann, Rimbach (DE); Eberhard Bock, Moerlenbach (DE)

(73) Assignee: Carl Freudenberg, Weinheim (DE)

( * ) Notice: Subject to any disclaimer, the term of this patent is extended or adjusted under 35 U.S.C. 154(b) by 77 days.

(21) Appl. No.: 09/642,361

(22) Filed: Aug. 21, 2000

(51) Int. Cl.7 .............................................. G01N 27/00
(52) U.S. Cl. ...................... 324/557; 559/711
(58) Field of Search .................. 324/557, 559, 324/71.1; 340/605, 604; 405/53, 54, 108; 417/63

(56) References Cited

U.S. PATENT DOCUMENTS

| | | | | |
|---|---|---|---|---|
| 4,543,525 A | * | 9/1985 | Boryta et al. ................ 324/559 |
| 4,569,634 A | * | 2/1986 | Mantell ........................ 417/63 |
| 4,719,407 A | * | 1/1988 | Converse et al. ............ 324/559 |
| 4,751,467 A | * | 6/1988 | Cooper ........................ 324/557 |
| 4,781,535 A | * | 11/1988 | Frawley et al. ................ 417/63 |
| 5,184,083 A | * | 2/1993 | Groover ...................... 324/559 |
| 5,560,279 A | * | 10/1996 | Connors et al. .............. 417/63 |
| 5,581,019 A | * | 12/1996 | Minor et al. .................. 73/115 |
| 5,850,144 A | * | 12/1998 | Howells et al. ............. 324/557 |
| 5,900,270 A | * | 5/1999 | Smith, III et al. ......... 324/71.1 |
| 2002/0021970 A1 | * | 2/2002 | Rohner ........................ 417/63 |

FOREIGN PATENT DOCUMENTS

| | | | | |
|---|---|---|---|---|
| DE | 3729726 | | 3/1989 | |
| EP | 0486618 | | 5/1992 | |
| EP | 0715690 | | 6/1996 | |
| JP | 2002/048671 | * | 2/2002 | .......... G01N/27/20 |

* cited by examiner

Primary Examiner—Michael Sherry
Assistant Examiner—Jermele Hollington
(74) Attorney, Agent, or Firm—Milde & Hoffberg, LLP

(57) ABSTRACT

Device to detect leaks and fatigue in membranes wherein the membrane consists of at least two membrane layers, and wherein at least one of the membrane layers includes a conductor on its inner surface that causes an alteration to a measured value in case of an alteration to either the membrane or the conductor.

20 Claims, 5 Drawing Sheets

DEVICE FOR DETECTING MEMBRANE LEAKS IN A DIAPHRAGM PUMP

Membranes enjoy widespread use. One frequent application is in machines having a hydraulic or pneumatic drive. In such machines, movement of the membrane transports a fluid. Membrane or diaphragm pumps are also widely used in the pharmaceutical, biological, and foodstuff industries. In such applications, a high degree of purity of the transported fluid is important. Another application field is the chemical industry, in which it is of primary importance that the transported fluid not leak out, since it may be poisonous, toxic, or flammable. In such applications, it is desirable, and sometimes necessary, that the membrane be constantly checked for integrity. Several mechanisms are known which perform this function.

The published German Patent Application No. DE OS 37 29 726 describes a membrane-machine unit that having at least two membranes which form a gap between them that is connected to a fluid leak sensor. If one or the other membrane is ruptured, the fluid enters the gap between the membranes, and the sensor reports the leak. Such a device is relatively inefficient in design, and problems may only be detected after a relatively large amount of fluid has leaked. Also, the effect may only be measurable after the closely-positioned membranes are forced apart by the leaking fluid.

Only then can the fluid reach the sensor. Additionally, the fluid must also reach the sensor's location.

The published European Patent No. EP 0 486 618 describes another arrangement for detecting a membrane fault wherein two membranes are mounted with a sensor between them to detect the presence of fluid between the membranes. Here also, the detection occurs only after a large quantity of fluid has entered the space between the two membranes. Additionally, the design of the membranes with the accompanying detector is very inefficient.

The European Patent No. EP 0 715 690 presents yet another method of detecting a damaged membrane. This patent provides a pump membrane that contains a layer of sealed, porous polytetrafluorethylene (PTFE) in which an electrically-conducting fiber made of expanded porous PTFE is embedded. The ends of the fiber are connected to an electrical measuring device. By measuring changes in conductivity of the fiber, fatigue or cracks in the membrane may be detected. This design has the disadvantage that it is very expensive to produce, and is therefore associated with high cost.

SUMMARY OF THE INVENTION

The principal object of the present invention is to provide a device to detect leaks or fatigue in membranes that is simple in design and may be produced at low cost.

This object, as well as other objects which will become apparent from the discussion that follows, are achieved, in accordance with the present invention, by constructing the membrane of two membrane layers to form a double membrane, and providing at least one of the membrane layers with at least one conductor that results in a change in measured value in response to any change in either the membrane or the conductor.

With such a membrane construction, optical devices used to detect fluid accumulations are no longer required, and it is also no longer necessary to embed an electrical conductor directly into a membrane layer. Along with an advantageous simplicity of manufacture, there is also the advantage that damage to the membrane, as well as the magnitude of the damage, may be detected quickly.

A very simple option exists of emplacing electrically-conducting metal conductors or elastomer loops. Loops may, for example, be arranged radially in the membrane. Other configurations are certainly possible.

Based on another implementation of the invention, an optical fiber consisting of a glass or plastic fiber might be added to a membrane layer. Such an optical conductor could be in the form of a closed spiral circuit or open conductor spiral with reflecting end.

The conductor might also consist of a channel mounted on a membrane layer that contains a fluid. The channel would be arranged concentrically around the membrane layer center.

In a particularly space-saving and easy-to-produce monitoring device according to the invention, the conductor comprises a conductive "fleece" material (a fabric of nonwoven material) or piece of elastomer. Thus, the entire surface of the pertinent membrane layer may be coated so that a very precise location of a fault could be determined. The fleece piece might be produced from a fleece containing carbon fiber. This would allow various configurations to be pressed out. Formation of the piece of fleece or elastomer as a fabric made of metallic or carbon fibers is a further possibility.

Another very useful implementation of the invention might include an elastomeric element containing metal or carbon particles that are imprinted onto the membrane layers using a silkscreen method. This would produce a particularly flat membrane.

Another advantageous implementation might be achieved by using an elastomer conductor formed from an electrically-conducting foil vulcanized onto the membrane layer.

This new membrane monitoring device would in principle be formed of two membrane layers, where at least one would contain a conductor on its inner surface that detects damage to the membrane and passes a signal to a measurement or signaling device attached to it. This results in a layered construction of the membrane consisting of membrane layer, conductor layer, and membrane layer in its simplest form. The membrane layers could be produced from materials suitable to the membrane application. One very useful implementation form, particularly when the membrane is used for foodstuffs or chemical products, would be achieved if the membrane layer in contact with the fluid being transported were made of PTFE (polytetrafluorethylene) and the exterior membrane layer were made of an elastomer. The PTFE membrane layer would be particularly resistant to aggressive chemical substances, while the elastomer membrane layer would be very flexible. If a leak occurred in the PTFE membrane layer, it would be detected via the monitoring conductor mounted on the inner side of that membrane layer and reported. The elastomer membrane layer would itself remain intact, fulfilling the function of a second barrier. The most advantageous form of the membrane would be achieved if the membrane were to consist of a double membrane made using a PTFE (or similar material) membrane layer and an elastomer membrane layer, wherein each membrane layer be coated on its inner surface with a layer of electrically-conducting material, and wherein the layers be separated from each other by an electrically-insulating porous fleece layer. Production of such a membrane is relatively simple, and the entire surface of the membrane would be coated so that even the most minor damage could be detected.

Mounting of the conductors onto each membrane layer could be achieved using various methods. Advantageous options include thermal adhesive, vulcanization, or similar methods.

For a full understanding of the present invention, reference should now be made to the following detailed description of the preferred embodiments of the invention as illustrated in the accompanying drawings.

DESCRIPTION OF THE PREFERRED EMBODIMENTS

Figure 1:
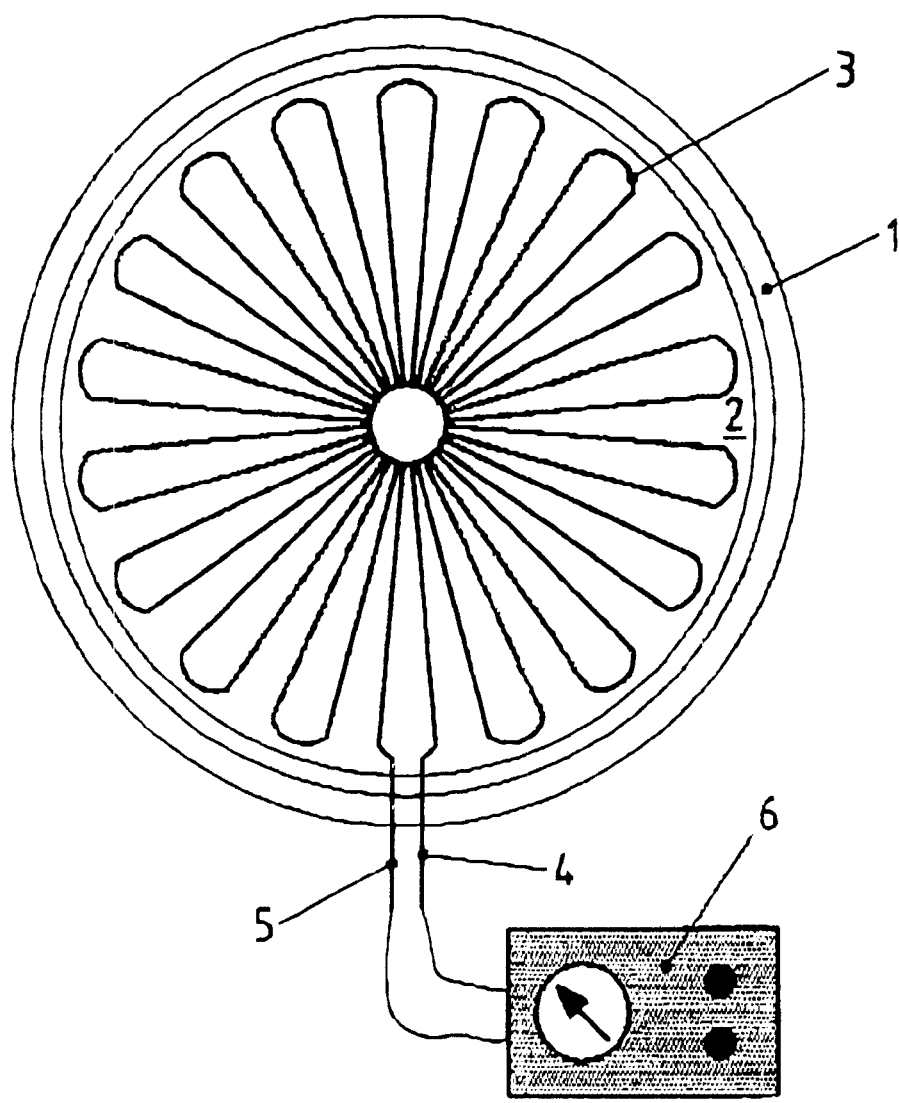
FIG. 1 is an overhead view of a membrane layer having metal conductor loops.

The preferred embodiments of the present invention will now be described with reference to FIGS. 1–5 of the drawings. Identical elements in the various figures are designated with the same reference numerals.

FIGS. 1 through 4 show membrane layers in overhead view that are configured with various conductors on their inner surfaces 2. FIG. 1 shows a conductor loop 3 mounted on the inner side 2 of the membrane layer 1 that is typically made of metal or an electrically-conducting elastomer. The loop 3 is arranged radially on the membrane layer 1. The ends 4 and 5 of the loop 3 are connected with the measuring device 6.

Figure 2:
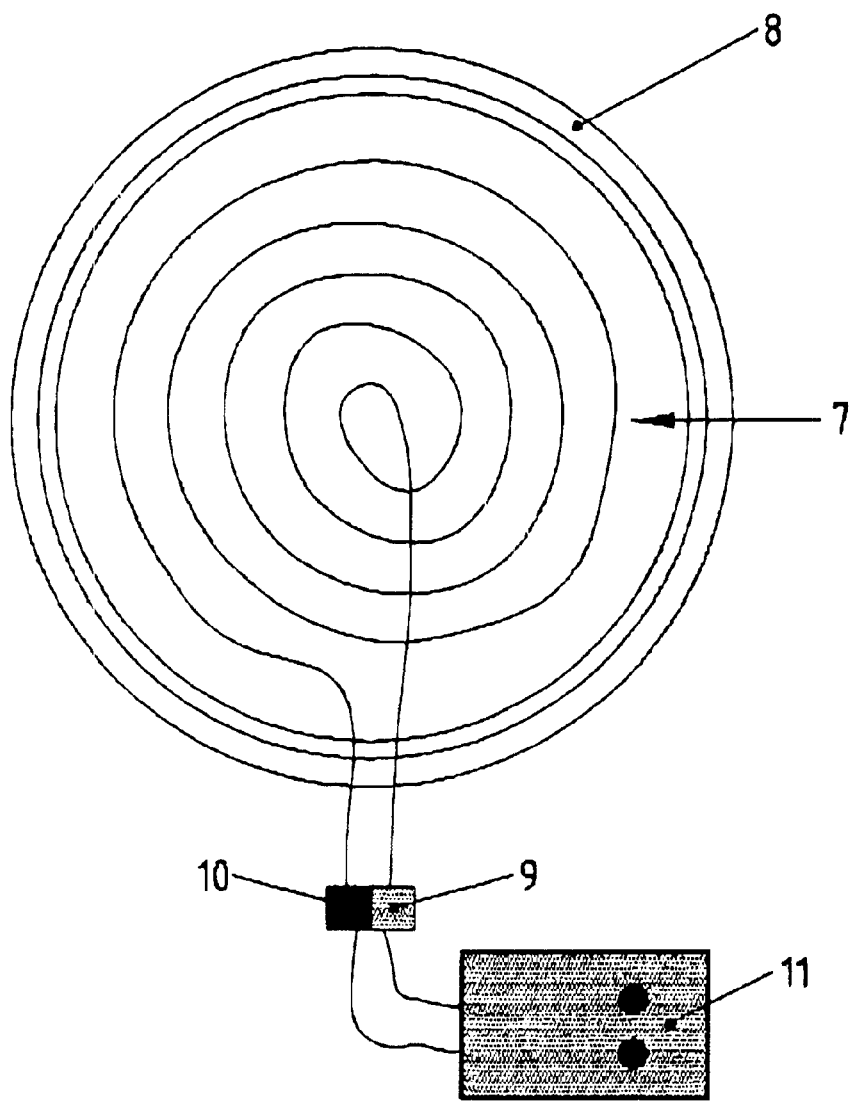
FIG. 2 is an overhead view of a membrane layer having a closed metal conductor spiral circuit.

FIG. 2 shows, instead of a loop, an optical conductor 7 mounted on a membrane layer 8. The optical conductor 7 is arranged in a spiral, and its ends are connected to the necessary optical devices. Device 9 sends out an optical signal that is received by device 10. The necessary measuring device 11 evaluates the signal, allowing detection of fatigue or damage to the pertinent membrane layer based on the light intensity.

Figure 3:
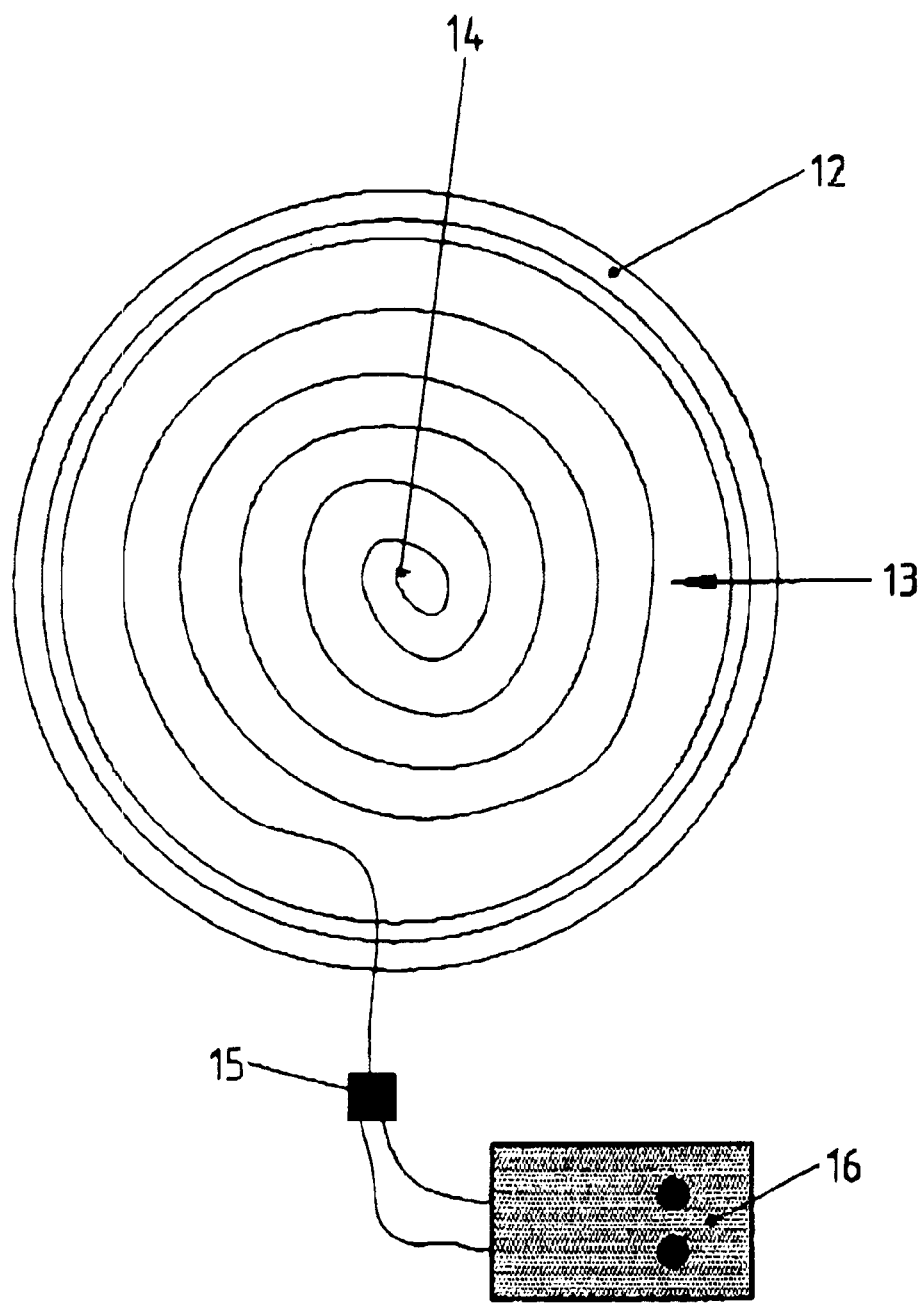
FIG. 3 shows a membrane layer with an open optical conductor.

FIG. 3 shows a membrane layer 12 equipped with an open optical conductor 13 that includes a reflective end 14. A corresponding optical device 15 serves to transmit and receive suitable optical signals that are processed and displayed using measurement device 16.

Figure 4:
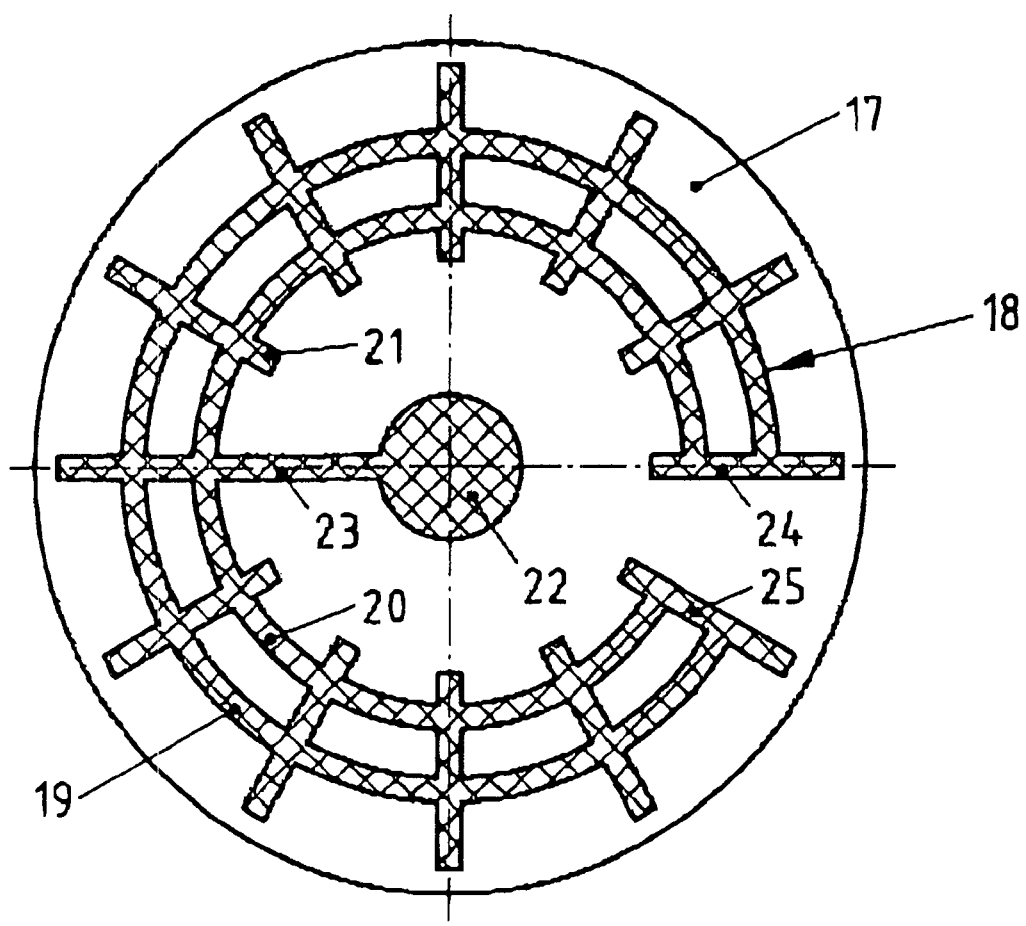
FIG. 4 shows a membrane layer with a fluid channel.

FIG. 4 shows a membrane layer 17 that includes a channel 18 for a fluid medium. The channel 18 consists of two concentric ring channels 19 and 20 with radially-arranged connecting channels 21 and a central basin 22 located in the center of the membrane layer that is connected with the ring channels 19 and 20 via radial channel 23. The ring channels 19 and 20 are not completely closed in this case, but rather are interrupted by the radial channels 24 and 25. The channels are connected to a measurement device that serves to detect a break to a channel.

FIGS. 1 through 4 each show the surface of a membrane layer on which the appropriate conductors are mounted. This membrane layer is preferably the one facing the medium being transported, and the conductors are arranged on the surface away from the medium.

Figure 5:
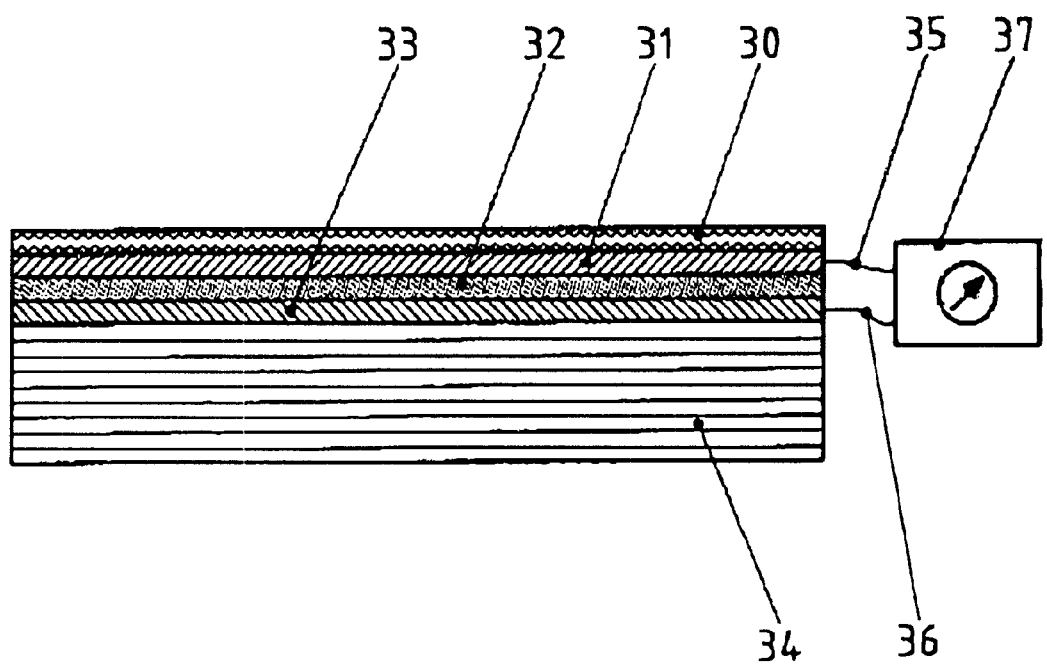
FIG. 5 shows a cross-section of a membrane composed of two membrane layers and two conductors.

FIG. 5 shows a cross-section of a membrane 1 having a layered construction. It consists of a membrane material 30 facing the medium, an electrically-conducting material 31, a fleece 32 as insulation layer, and a second electrically conducting layer 33 that is connected to the second membrane layer 34 by means of an elastomer material. Such a membrane may be very easily constructed by combining the individual layers using thermal adhesive or vulcanization. The two electrically-conducting layers 31 and 33 are connected with the measuring device 37 via outputs 35 and 36. In case of a tear to the membrane, an electrically-conducting fluid is forced into the non-conducting fleece 32, and the high resistance between the conducting layers 31 and 33 is neutralized. The membrane tear is indicated by the measurement device 37.

There has thus been shown and described a novel device for detecting leaks in membranes which fulfills all the objects and advantages sought there for. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a device for detecting leaks and fatigue in a membrane for a diaphragm pump, wherein the membrane consists of at least two membrane layers, each having an inner surface arranged in adjacent, facing relationship to the inner surface of the other membrane layer, the improvement comprising at least one conductor disposed on and adhered to the inner surface of at least one of the membrane layers, said conductor exhibiting a change in a measured value in response to any change in either the membrane or the conductor.

2. Device according to claim 1, wherein the conductor is formed from a fabric having metallic fibers.

3. Device according to claim 1, wherein the conductor is formed from a fabric having carbon fibers.

4. Device according to claim 1, wherein one of the membrane layers consists of PTFE (Teflon) and wherein another membrane layer consists of an elastomer.

5. Device according to claim 1, wherein said at least one conductor is adhered to the inner surface of the at least one membrane layer by means of a thermal adhesive or by vulcanization.

6. Device according to claim 1, wherein the conductor mounted on the membrane layer is an electrically-conductive elastomeric loop.

7. Device according to claim 6, wherein the elastomeric loop extends radially on the membrane layer.

8. Device according to claim 1, wherein the conductor mounted on the membrane layer is an electrically-conductive metal loop.

9. Device according to claim 8, wherein the metal loop extends radially on the membrane layer.

10. Device according to claim 1, wherein the conductor includes a piece of conductive fleece.

11. Device according to claim 10, wherein the piece of fleece consists of carbon fiber fleece.

12. Device according to claim 10, wherein the piece of fleece is formed from a fleece sheet.

13. Device according to claim 1, wherein the conductor includes a piece of conductive elastomer.

14. Device according to claim 13, wherein the piece of elastomer contains metal particles that are imprinted on the membrane layer using a silkscreen process.

15. Device according to claim 13, wherein the piece of elastomer contains carbon particles that are imprinted on the membrane layer using a silkscreen process.

16. Device according to claim 13, wherein the elastomer conductor comprises an electrically-conductive elastomer foil that is vulcanized onto the membrane layer.

17. Device according to claim 1, wherein each membrane layer is coated with an electrically-conducting layer on its inner side, and wherein the layers are separated by an electrically-insulating porous layer.

18. Device according to claim 17, wherein one of the membrane layers consists of PTFE (Teflon) and wherein the other membrane layer consists of an elastomer.

19. Device according to claim 17, wherein the porous layer is made of fleece.

20. Device according to claim 1, further comprising measuring means, coupled to said at least one conductor, for detecting a change in either the membrane or the conductor.

* * * * *